United States Patent
Lettman et al.

(10) Patent No.: US 10,943,506 B2
(45) Date of Patent: Mar. 9, 2021

(54) RESETTABLE PREFILLED SYRINGE TRAINING DEVICE WITH RELEASEABLY LOCKING NEEDLE GUARD

(71) Applicant: NOBLE INTERNATIONAL, INC., Orlando, FL (US)

(72) Inventors: Jeffery A. Lettman, Orlando, FL (US); Tingting Liu, Orlando, FL (US)

(73) Assignee: Noble International, Inc., Orlando, FL (US)

( * ) Notice: Subject to any disclaimer, the term of this patent is extended or adjusted under 35 U.S.C. 154(b) by 512 days.

(21) Appl. No.: 15/803,330

(22) Filed: Nov. 3, 2017

(65) Prior Publication Data
US 2018/0233066 A1 Aug. 16, 2018

Related U.S. Application Data

(63) Continuation-in-part of application No. PCT/US2016/046639, filed on Aug. 11, 2016.
(Continued)

(51) Int. Cl.
*G09B 23/28* (2006.01)
*A61M 5/178* (2006.01)
(Continued)

(52) U.S. Cl.
CPC ........... *G09B 23/285* (2013.01); *A61M 5/178* (2013.01); *A61M 5/31578* (2013.01);
(Continued)

(58) Field of Classification Search
None
See application file for complete search history.

(56) References Cited

U.S. PATENT DOCUMENTS

| 1,114,100 A | * | 10/1914 | Blomberg | ............. A47G 33/12 |
| | | | | 248/526 |
| 5,318,547 A | | 6/1994 | Altschuler | |

(Continued)

FOREIGN PATENT DOCUMENTS

| WO | 2005/009519 | 2/2005 |
| WO | 2014/154795 | 10/2014 |

(Continued)

OTHER PUBLICATIONS

International Search Report and Written Opinion for PCT Application PCT/US16/046639 dated Dec. 22, 2016, pp. 1-13.
(Continued)

*Primary Examiner* — James B Hull
*Assistant Examiner* — Jennifer L Korb
(74) *Attorney, Agent, or Firm* — Timothy H. Van Dyke; Wolter Van Dyke Davis, PLLC

(57) ABSTRACT

In an embodiment, a resettable injection training device and a method embodiment for resetting the device is provided herein. The device may include a housing having a proximal end and a distal end, the housing defining a cavity there within. A plunger may be slidable relative to the housing between the proximal end and the distal end. A releasably locking shield having a proximal end and a distal end, and being slidably engaged with the housing is also provided. The shield may be slidable between a retracted, pre-use position an extended, locked, post-use position. The device may further include a flat biasing member for locking the shield in the extended position, and a compressing component slidable relative to the housing, wherein pressure on the flat biasing member from the compressing component deforms the flat biasing member, and unlocks the shield, and wherein a release of pressure by the compressing component
(Continued)

on the flat biasing member locks the shield in an extended, post-use position.

14 Claims, 9 Drawing Sheets

Related U.S. Application Data

(60) Provisional application No. 62/203,863, filed on Aug. 11, 2015.

(51) Int. Cl.
  *A61M 5/315* (2006.01)
  *A61M 5/32* (2006.01)
  *A61M 5/31* (2006.01)

(52) U.S. Cl.
  CPC ........ *A61M 5/3202* (2013.01); *A61M 5/3221* (2013.01); *A61M 5/315* (2013.01); *A61M 5/3148* (2013.01); *A61M 5/3204* (2013.01); *A61M 5/326* (2013.01); *A61M 5/3243* (2013.01); *A61M 5/3286* (2013.01); *A61M 2005/3261* (2013.01); *A61M 2005/3265* (2013.01)

(56) References Cited

U.S. PATENT DOCUMENTS

| | | | |
|---|---|---|---|
| 5,344,407 A | 9/1994 | Ryan | |
| 7,220,247 B2 | 5/2007 | Shaw et al. | |
| 10,417,937 B2* | 9/2019 | Gaillot | G09B 23/285 |
| 2007/0111175 A1* | 5/2007 | Raven | G09B 23/285 |
| | | | 434/262 |
| 2016/0293058 A1 | 10/2016 | Gaillot et al. | |
| 2017/0148354 A1 | 5/2017 | Baker et al. | |

FOREIGN PATENT DOCUMENTS

| | | |
|---|---|---|
| WO | 2014154795 A1 | 10/2014 |
| WO | 2014164948 A1 | 10/2014 |
| WO | 2017027753 A1 | 2/2017 |

OTHER PUBLICATIONS

BD, "BD Safety and Shielding Systems", brochure, 2 pages (2017).
International Search Report and Written Opinion for PCT/US18/59204; dated Feb. 7, 2019, 17 pages.
Extended European Search Report for EP16835945.3; dated Feb. 12, 2019; 7 pages.
CN201680057916.8; Office Action; dated Nov. 14, 2019 15 pages.

* cited by examiner

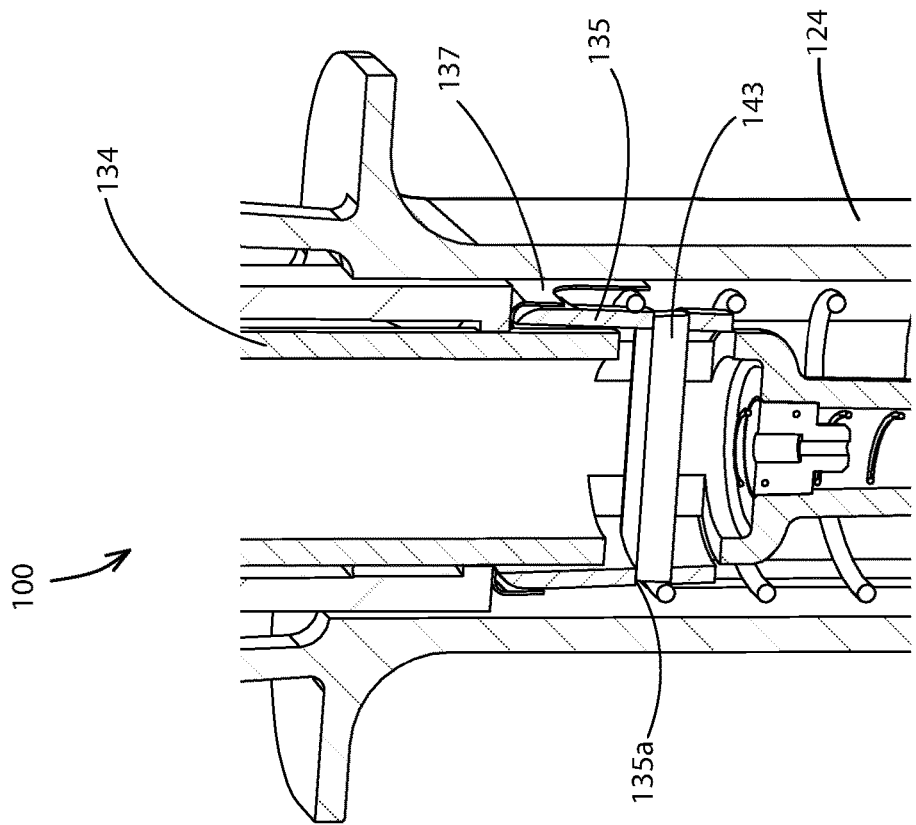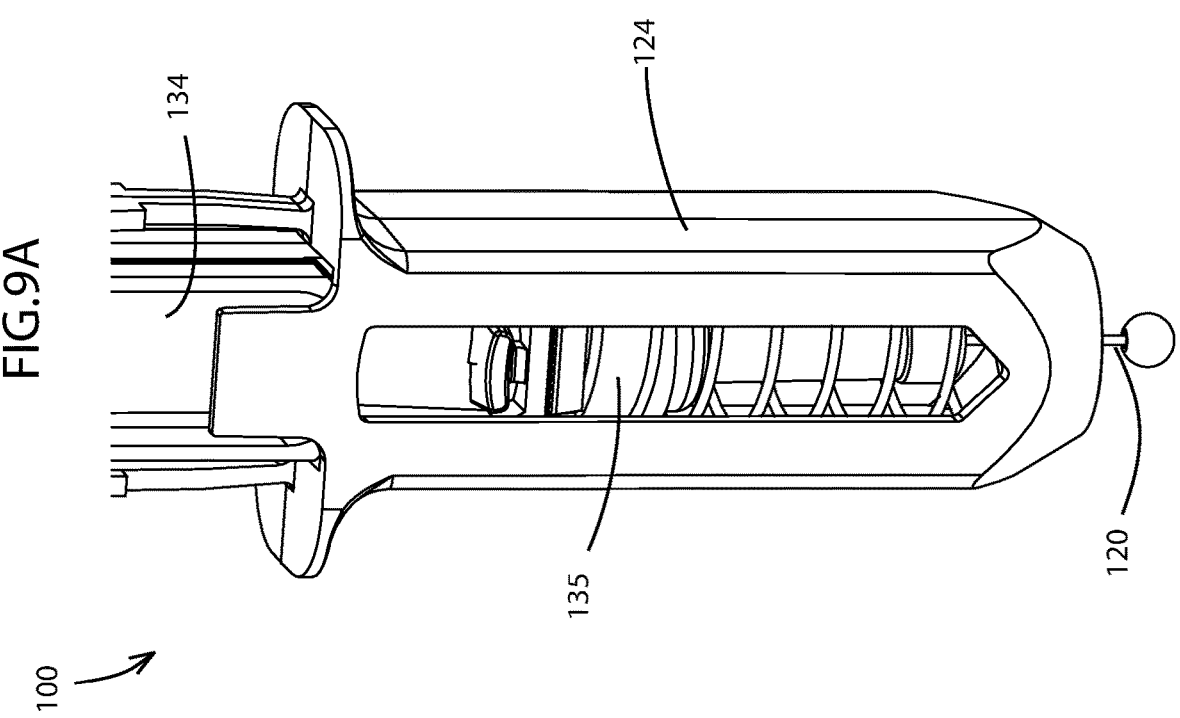

RESETTABLE PREFILLED SYRINGE TRAINING DEVICE WITH RELEASEABLY LOCKING NEEDLE GUARD

CROSS-REFERENCE TO RELATED APPLICATIONS

This application is a continuation in part application of International Application No. PCT/US16/46639 filed Aug. 11, 2016, which claims priority to U.S. Provisional Application No. 62/203,863, filed Aug. 11, 2015, both of which are incorporated by reference herein.

BACKGROUND

Injection devices have recently become increasingly popular for single dose or multi-dose, at home self-administration. These devices include both auto-injection devices and pre-filled syringe devices, and are often designed to accomplish two basic objectives: convenience of drug delivery in an outpatient or at home setting, and/or automation of drug delivery in an outpatient or at-home setting. These devices may be mechanically spring-loaded devices that advance a plunger or rubber stopper to transfer medication via hollow-bore needle to a patient's tissues, in some examples. These devices lack the ability to regulate whether the medication is actually delivered to the patient or whether it is delivered to a correct location. Most of these devices fail to integrate advanced digital capabilities.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

An additional concern exists with regard to injection devices is that users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self-administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery. In many cases, unfamiliarity with the way in which a particular injection device functions is the cause of concern an anxiety in users, and oftentimes the cause of mistakes when using the device.

Safe use and re-use of these training devices requires resetting of the devices by way of a mechanism that provides the movement of the device to initiate the injection, and in some instances, the portion of the device that protects users from sticking themselves. Therefore, a device which allows repeated practice and use to enhance familiarity with the injection device and the self-injection process, along with the ability to safely and efficiently reset the device is paramount to an effective device for injection training.

SUMMARY

In an embodiment, a resettable injection training device is provided. The device may include a housing having a proximal end and a distal end, the housing defining a cavity there within. A plunger may be slidable relative to the housing between the proximal end and the distal end. A releasably locking shield having a proximal end and a distal end, and being slidably engaged with the housing is also provided. The shield may be slidable between a retracted, pre-use position an extended, locked, post-use position. The device may further include a flat biasing member for locking the shield in the extended position, and a compressing component slidable relative to the housing, wherein pressure on the flat biasing member from the compressing component deforms the flat biasing member, and unlocks the shield, and wherein a release of pressure by the compressing component on the flat biasing member locks the shield in an extended, post-use position.

In another embodiment, a method for resetting a resettable injection training device with an extended, locked shield is provided. The device includes a housing, a plunger disposed and slidable within a cavity of the housing, and a compressing component for interfacing with a locking member having locking arms. The method includes sliding the plunger in a proximal direction to retract the plunger, wherein reset of the plunger causes the compressing component to interface with the locking member and the locking arms to release contact with the shield, the method further includes sliding the shield from the extended position to a retracted position.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 9A is a side view of a portion of the device shown in FIG. 7A.

FIG. 9B is a cross sectional view of the device shown in FIG. 9A.

DETAILED DESCRIPTION

Figure 1:
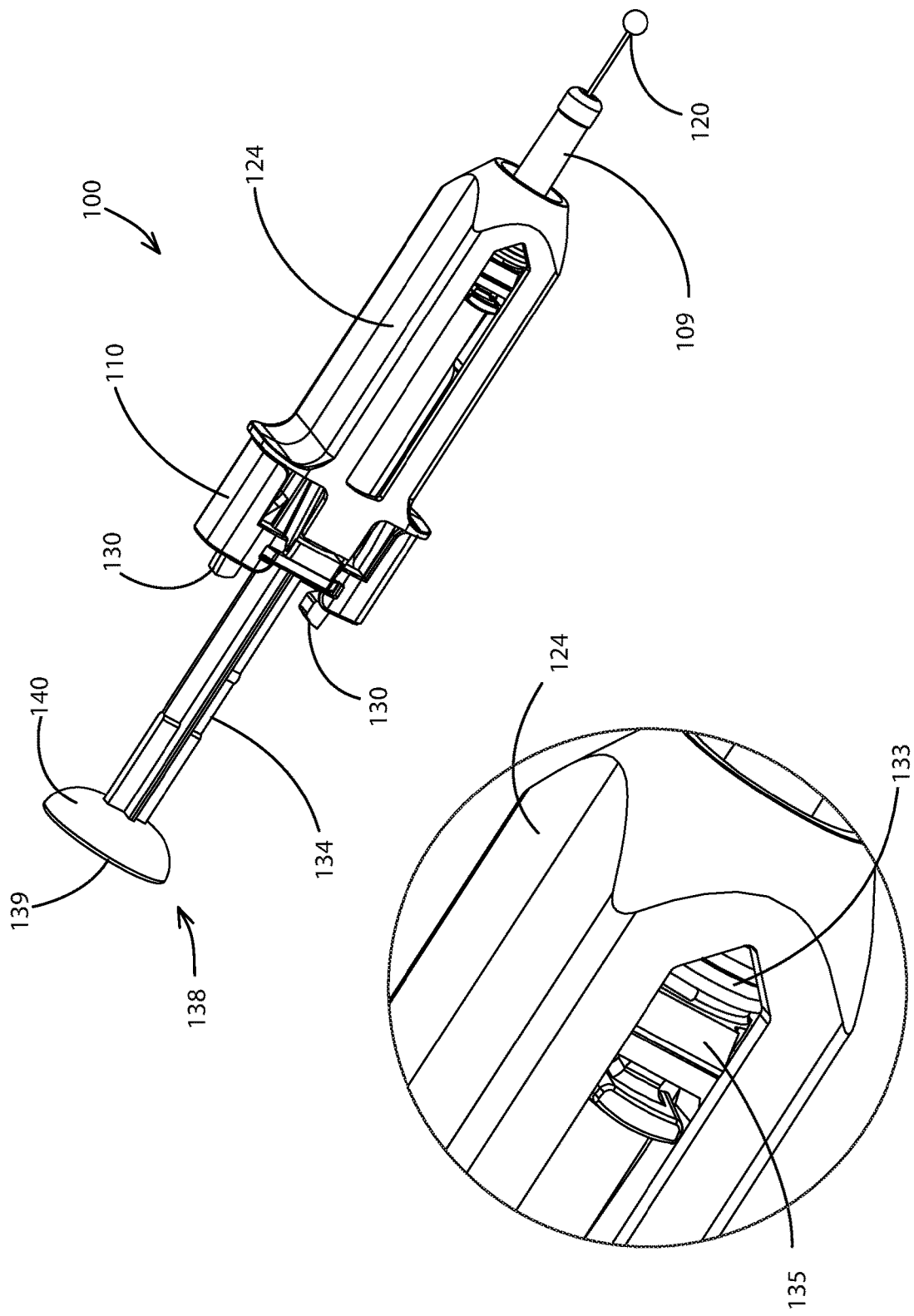
FIG. 1 is a perspective view of an embodiment of a resettable injection training device, and a zoomed in view of a portion of the embodiment

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable. The term "adjacent" as used herein, includes but is not limited to near, associated with, or in close proximity to.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

Those skilled in the art will understand that the term gauge (G) refers to a gauge of a needle according to gauges known in the art. Typical gauge ranges used in the equation(s) provided herein will include gauges ranging between approximately 18-30.

The inventors herein have identified a need for a device to be used in effectively training patients to use a needle-containing injection device, particularly when these injection devices are used for at home or outpatient environments. In the field of medicament injection training devices, correct injection of medicament by way of the injection device is crucial for obtaining accurate doses of medicament contained therein. Factors such as a fear of needles, fear of pain associated with an injection, inexperience with injection devices and delivering injections, and unfamiliarity with injection devices and their operation, among other factors can contribute to issues in administering the medicament correctly with the injection device. Consequently, patient training in correct operation of the injection device is crucial to reducing patient anxiety and enhancing patient compliance.

During an injection, a user of an injection device having a needle encounters various forces. Oftentimes, the first force encountered is that which is required to traverse a first layer of tissue (oftentimes the skin) with the needle, the pressure required by the user on the needle until the needle traverses the user's first layer of tissue is called a deformation force, which is the force that deforms the skin until the needle punctures the skin. This force required increases as the skin becomes deformed. Following the deformation force, there is often a temporary and typically brief decrease in force on the needle during an injection, known as the puncture force, which is the force that occurs once the needle has traversed the skin, i.e., punctured the skin, and before the needle moves further into the tissue of the patient. A third force often encountered during an injection follows the puncture force, and is termed an insertion force. The insertion force is an increasing force on the needle as the needle traverses tissue of the patient to reach a target location in the patient required for the injection. The increase in force over time typical of the insertion force period occurs as the needle travels through the tissue and can be attributed to an increase in pressure on the needle as it passes through multiple layers of tissue on its trajectory to the target injection location in the patient. These forces are often surprising and unexpected to an inexperienced injection provider, whether it is a patient who is self-administering an injection or a medical personnel administering an injection to a patient. Embodiments of the invention as described herein are provided to accurately simulate these forces, among other features of an injection and an injection device to decrease anxiety associated with administering an injection.

In an embodiment, a injection simulation member is provided to allow for a simulated injection experience without puncturing the skin of a user. The resettable injection training device may include an injection simulation member which may have a blunt end probe or other similar object known in the art provided to mimic the sound, look, and/or feel of the injection by an injection member (i.e., needle, for example) in a training or simulation session allowing a user to train oneself for administering an injection without puncturing the skin of the user. One skilled in the art would realize that the injection simulation member can be made of any materials known in the art to, in some embodiments, provide a flexibility, and tensile modulus to simulate a needle while maintaining the rigidity and stability to provide a simulated sensation of an injection without traversing the skin of a user. The resettable injection training device provides a perception to a user of injection into the skin and mimics or simulates an actual injection during retraction of the injection simulation member from an extended position to a retracted position, in some embodiments, upon application of a force, to simulate an injection without traversing or puncturing the skin of the user.

Embodiments of the resettable injection training device may provide tactile, visual, and auditory stimuli to a user, wherein during use of the device, the tactile, visual, gustatory, olfactory, or auditory feedback, or any combination thereof, are synchronized in a manner such that a needle-containing injection delivery device is accurately simulated. The synchronization of the stimuli is a significant factor in facilitating multisensory learning of the user.

The injection simulation device embodiments described herein may include components which provide a tactile/force reflecting mechanism (i.e., resistance mechanism) to provide force feedback to simulate the feel of an injection device used during an injection. Force feedback is typically accomplished by a tactile/force reflecting mechanism that imparts force to a user of the injection simulation device in response to manipulation of the injection simulation device. The force(s)/resistances that may be generated as a user manipulates the injection simulation device against a surface simulate the forces/resistances encountered during an injection at a target location of a user.

Multiple forces are encountered during an injection, and these forces are often influenced by one or more variables including needle gauge, needle length, injection angle needle point, needle coating or other surface characteristics, lubrication of needle or injection site, needle depth in patient tissue, type of patient tissue (i.e., skin, muscle), characteristics of patient tissue which may be influenced by age, health, weight, and/or genetically determined variables, among other potential force-influencing variables.

Forces that may be encountered during an injection are simulated in embodiments of the injection simulation device provided herein. Forces that may be encountered during an injection include a deformation force, a puncture rebound force, an insertion force, a relaxation force, and an extraction force or any combination thereof. A deformation force may occur when a needle is pressed onto a surface of a tissue, for example, an outer surface of the epidermal layer of a patient, causing the epidermis to deform under the pressure of the needle prior to puncture of the epidermis by the needle. A puncture rebound force refers to the force that is sensed once the needle traverses the tissue of the subject. It has been discovered that this causes a temporary decrease in force during an injection. An insertion force can be described as the force of the injection after the needle traverses the tissue, and until the needle reaches its target depth in the patient tissue. In some instances, the insertion force is the greatest increase in force over time during the course of an injection. A relaxation force typically follows the insertion force. The relaxation force occurs once the needle has reached its target depth in the patient tissue and the medicament is injected into the target tissue. The relaxation force is marked by a decrease in force that occurs as the medicament is expelled through the needle. An extraction force is one which is felt during removal or retraction of the needle from the tissue, and is marked by a greater decrease in force over time than the relaxation force, in some non-limiting instances.

Embodiments of the resistance mechanism described herein may include different components in different embodiments. In non-limiting embodiments, the resistance mechanism may include multiple components, such as, a combination of structural features of the injection simulation member which may move relative to one another to produce a resistance during a simulated injection which mimics the forces encountered by a user during an injection with an training device, for example. The resistance produced may be controlled by manipulating the shape(s) of one or more of the structural features, or the surface(s) characteristics of the one or more structural features, or the material(s) of the one or more structural features, in non-limiting embodiments.

The resistance mechanism may alternatively include a material traversable by a needle, for example, to produce a varying resistance to mimic the forces and the tactile feel of an injection. This traversable material may be disposed within the housing of the injection training device or on an outer portion thereof. Traversal of the needle through the traversable material may provide a tactile feel of a needle traversing a tissue of a subject during an injection. Furthermore, the traversal may be viewable by the user of the device, providing a visual and tactile representation to simulate an injection event. The material may include a rubber or septum material, or a pseudo-skin material, in non-limiting embodiments, to further enhance the simulation of penetrating tissue.

In one embodiment, the injection simulation member may configured to simulate a needle of an injection device with a determined gauge (G) and which device is configured such that the injection simulation member retracts from an extended position to a first retracted position under application of a force 1 (N), to simulate a deformation force (Forced) according to the formula Forced=C (−0.046(G)+ 1.83), wherein the force value ranges between +/−1%-30% and every integer in between, and wherein C comprises a coefficient, said coefficient being a factor of the deformation force of the injection simulation device. In another embodiment, the force value ranges +/−1%-20% and every integer in between. In yet another embodiment, the force values ranges +/−1%-10% and every integer in between. The value of C is further defined below. In one non-limiting embodiment, the value of C may include a value between 0.2-3.6.

In a further embodiment, the retraction of the injection simulation member from the extended position to the first retracted position comprises a force determined by the formula F(x)=K*XP wherein F(x) is a force value at a point between the fully extended position and the first retracted position, K is a resistance value including a resistance of the injection simulation device, X is a displacement value, and P is an exponential power value greater than zero. F(x) may be a force value simulating a deformation force in one embodiment. In another embodiment, F(x) may be a force value simulating an insertion force.

In an alternative non-limiting embodiment, F(x) is a force value at a point between the fully extended position and at least a second retracted position. F(x) denotes F as a function of (x). In non-limiting embodiments described herein, F(x) denotes a Force at point x.

In another embodiment, the injection simulation device is provided wherein the deformation force Fd depends on one or more factors including: a composite area of injection value (C1), a bevel of the needle value (C2), lubrication of the needle or an injection site value (C3), and/or injection angle (C4) wherein a force of the device is determined by the formula C=C1*C2*C3*C4.

In one embodiment, the C1 value includes a higher value when the composite area of injection includes a denser tissue area and a lower value when the composite area of injection includes a less dense tissue area. For example, muscle tissue includes a denser tissue than in adipose tissue; consequently, the C1 value would be higher for muscle tissue than it would be for adipose tissue. In one non-limiting example, when the composite area of injection includes a subcutaneous tissue, the C1 value ranges from 0.5-2.0.

In a further embodiment, the injection simulation device may be configured to simulate a force based on a needle bevel, wherein the C2 value is higher when a needle with a bevel that creates a larger angle at a distal end of the needle is simulated, and lower when a needle with a bevel that creates a smaller angle at the distal end of the needle is simulated. In a non-limiting example, the C2 value ranges from between 0.5-1.5.

In still a further embodiment, the injection simulation device may be configured to simulate a force based on lubrication or non-lubrication of a needle or an injection site, and wherein the C3 value is higher when an un-lubricated needle and/or injection site is simulated and lower when a lubricated needle and/or injection site is simulated. In one non-limiting example, the C3 value ranges from between 0.5-1.0.

In yet a further embodiment, the C4 value decreases when a longitudinal axis of the injection simulation member is generally perpendicular to a plane in which a surface including the injection site is disposed, and increases when an angle between the longitudinal axis of the injection simulation member and the plane in which the surface including the injection site decreases. In a non-limiting example, the C4 value includes 1.0 when the angle between the longitudinal axis of the injection simulation member and the plane of the surface including the injection site comprises 90 degrees. In another non-limiting example, the C4 value includes 1.4 when the angle between the longitudinal axis of the injection simulation member and the plane of the surface including the injection site comprises 45 degrees.

The exponential value, P, is a value that may affect the change in force exponentially, where as the P value increases, the force value may increases exponentially. In a non-limiting embodiment, the P value may range between 0.5 and 4.

The displacement value, X, is a position of the injection simulation member as it moves between extended and retracted positions. In one non-limiting embodiment, the X value ranges between 0.000001 mm and 250 mm.

In an embodiment, an injection training device for simulating one or more forces of an injection may include a retractable injection simulation member configured to simulate a needle of an injection device with a determined gauge. The device is configured such that the injection simulation member retracts from an extended position to a retracted position upon application of a force according to a multi-phase force profile. The multi-phase force profile may include at least a first phase configured to simulate a deformation force, the deformation force simulating the force of pressing a needle against a subject so as to deform at least a first layer of tissue prior to puncturing at least the first layer of tissue of the subject; and at least a second phase configured to simulate a puncture rebound force, in a non-limiting embodiment. In one embodiment, the second phase includes a force that is less than the deformation force.

The device may further include at least a third phase configured to simulate an insertion force, wherein the insertion force includes the force required for a needle to traverse the tissue to a target injection location of the subject. The target injection location includes a location wherein the injection is to occur, such as, muscular tissue, intra-ocular tissue, subcutaneous tissue, adipose tissue, intra or inter peritoneal tissue, inter or intra venous or arterial tissue, among other target locations for injections known to those skilled in the art.

In a further embodiment, the injection simulation device includes one or more additional phases configured to simulate puncturing of composite tissue areas. Composite tissue areas may include multiple layers of tissue that may be traversable, wherein multiple deformation, puncture, and insertion forces are required to reach the target location for the injection. Certain procedures such as an amniocentesis, for example, used in prenatal diagnosis of chromosomal abnormalities, fetal infections, or sex determination from a sample of amniotic fluid containing fetal tissues retrieved from the amniotic sac using a needle in the procedure, require passage through multiple layers of tissue to reach the target location. These procedures may include multiple phases and multiple forces which are experienced and which may be simulated in embodiments of the injection simulation device provided herein.

Turning to the Figures, FIG. 1 is a perspective view of an embodiment 100 of a resettable injection training device having a housing 110 (shown also in FIG. 3) and a shield 124 (shown also in FIG. 2) movable relative to the housing 110. The housing 110 includes a proximal end 112 and a distal end 114. A cavity 116 is defined within the housing 110. The shield 124 also includes a proximal end 113 and a distal end 115. An injection simulation member 120 extends from the distal end housing 114. The injection simulation member 120 may be associated with an injection simulation member biasing member (not shown in FIG. 1), so that the injection simulation member may extend and retract upon a force at its distal end, i.e., upon pressing the injection simulation member 120 against a target surface of a user during training, to simulate an injection. The injection simulation member biasing member may be disposed within a distal portion of the inner housing 109, in one non-limiting example.

Figure 5A:
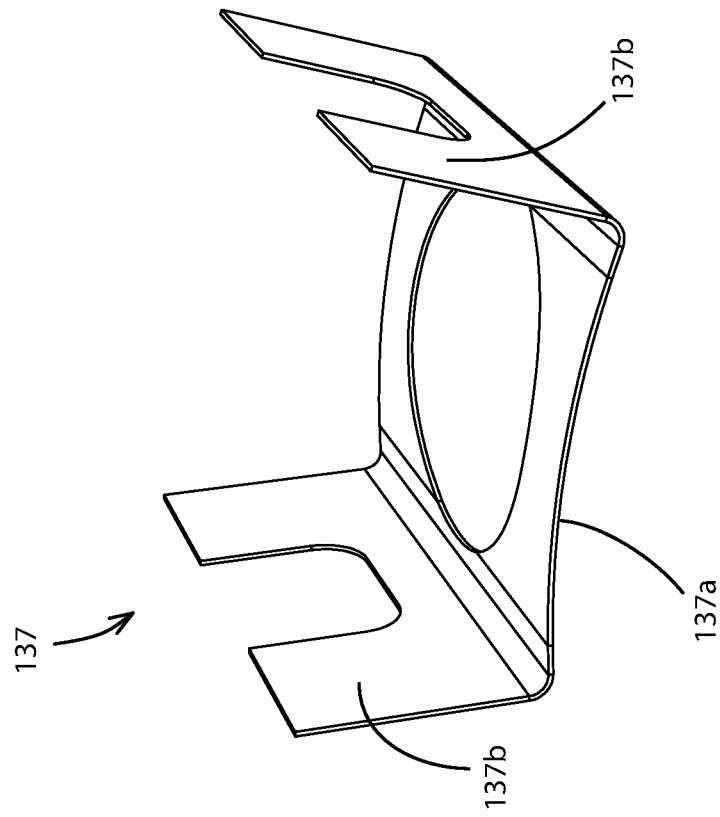
FIG. 5A is a perspective view of a flat biasing member component of an embodiment of the device.
Figure 5B:
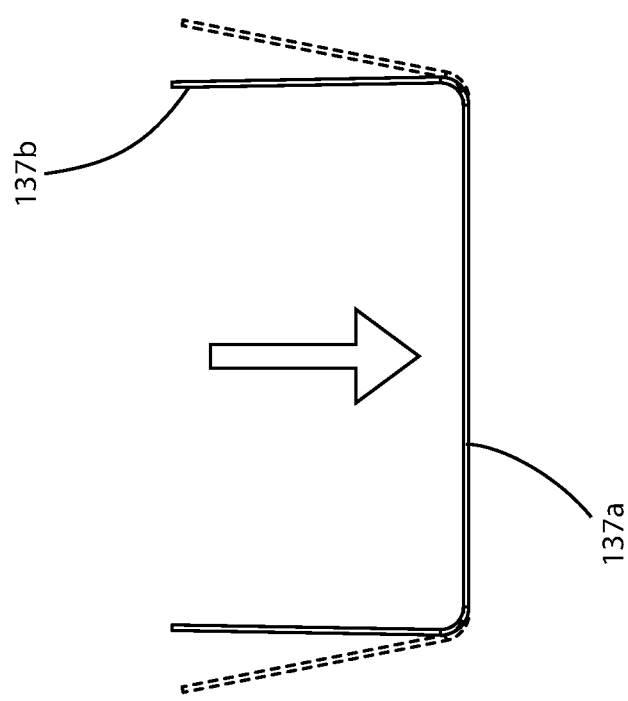
FIG. 5B include side views of the flat biasing member component of FIG. 5A/

A plunger 134 may be slidable within the cavity 116 between the proximal end 112 and the distal end 114 in the device embodiment 100. A reset biasing member 133 may be disposed between the shield 124 and the housing 110 as shown in FIG. 1. A compressing member 135 is associated with the compressing member 135. The compressing member 135 is also associated with the distal end of the plunger 134. Movement of the plunger 134 toward the distal end of the device compresses the reset biasing member 133 (as shown in FIG. 6C) and allows the compressing member 135 to shift distally, away from a flat biasing member 137 disposed proximal to the compressing member 135. When the device 100 is in a pre-use position, as shown in FIG. 1, and the plunger 134 is retracted, the compressing component 135 upon force by the reset biasing member 133 with the shield 124 in a pre-use position, the compressing component 135 presses against the flat biasing member 137 causing it to deform slightly as generally shown in FIG. 5B. The flat biasing member 137 includes a body portion 137a, with locking arm portions 137b. As shown in FIG. 5A-C, upon pressure on the biasing member body portion 137a, the flat biasing member 137 is deformed such that locking arm portions 137b shift inward, and away from the shield 124.

Figure 2:
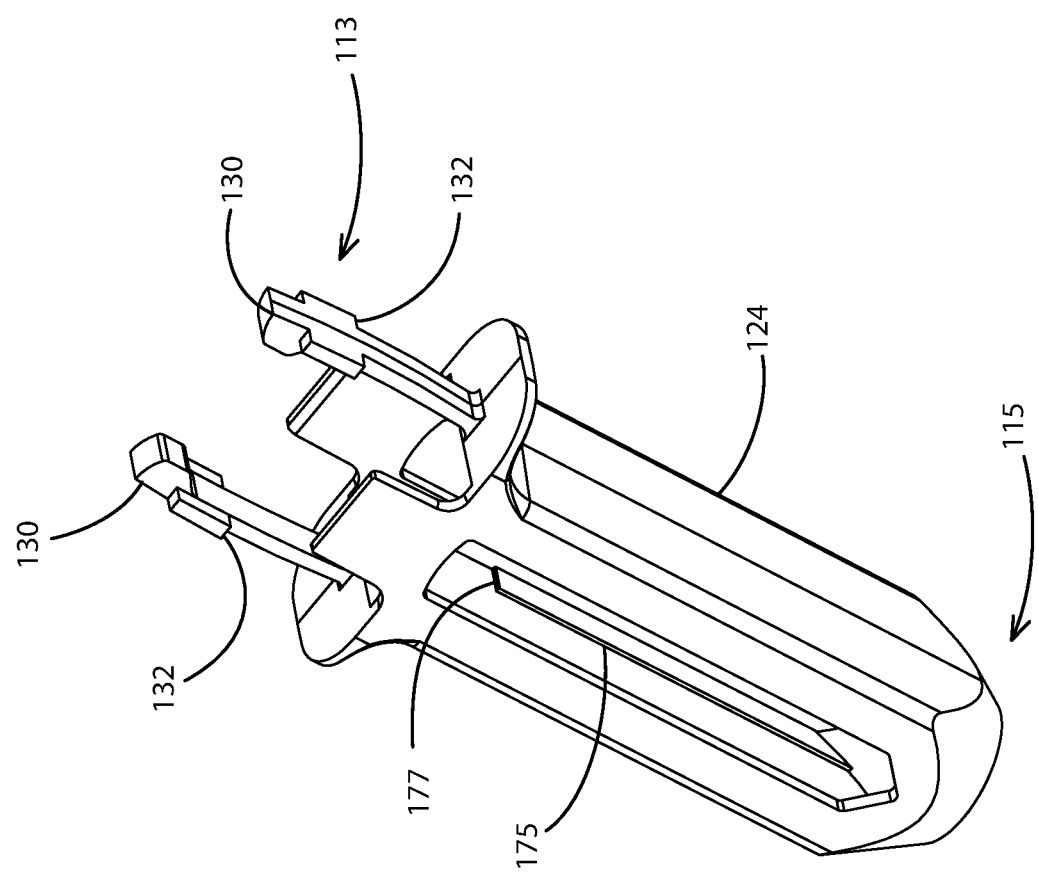
FIG. 2 is a side perspective view of a shield embodiment.

FIG. 2 is a perspective view of the shield 124 having a proximal end 113 and a distal end 115. The shield 124 defines a cavity 175 for receiving the housing 110 there within, in a non-limiting embodiment. The shield 124 and the housing 110 may slide relative to one another, in a non-limiting embodiment. An inner surface of the shield 124 reveals one or more notches 177 for interfacing with the flat biasing member locking arms 137b.

Figure 3:
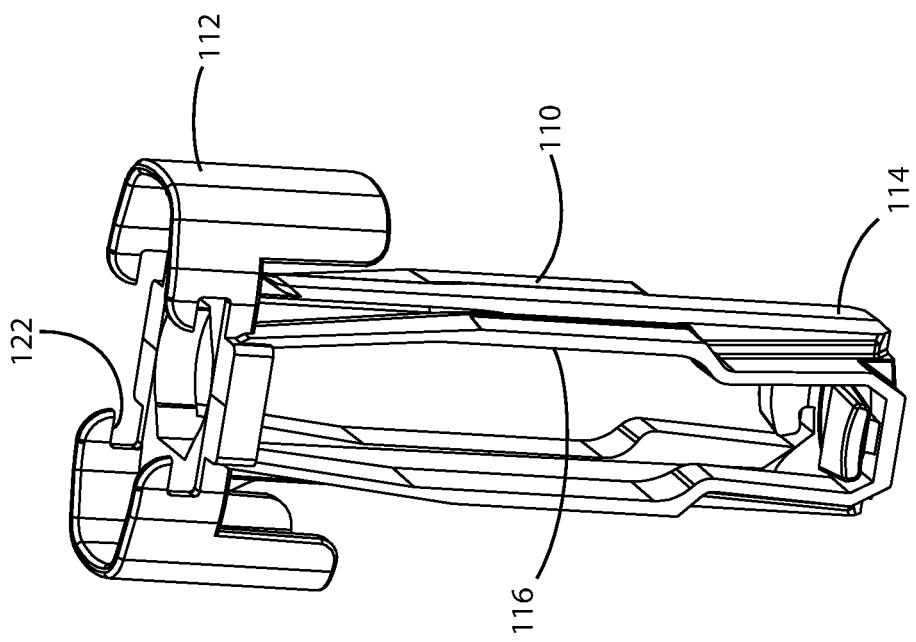
FIG. 3 is a side elevational view of an embodiment of the housing.

FIG. 3 is a side elevational view of the housing 110 having a proximal end 112 and a distal end 114. The housing 110 forms a cavity 116 for receiving a plunger 134 (not shown in FIG. 3) there within. The cavity 116 of the housing 110 may also accommodate an inner housing portion 109 (inner housing portion shown in FIG. 8A) for receiving the plunger 124 slidable there within. The housing 110 further includes one or more housing locking surfaces 122 for interfacing with the proximal end of the shield 124, when the shield is in a retracted position. More specifically, the proximal end of the shield 124 may include one or more arms 134 having one or more arm locking surfaces 132 to interface with the housing locking surfaces 122 to maintain the shield 124 in a reset or pre-use position until actuating the device 100, in one non-limiting embodiment.

Figure 4:
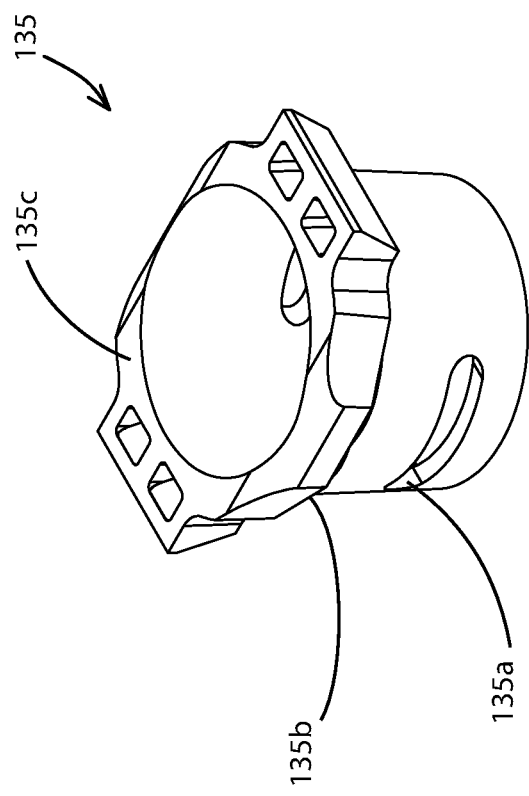
FIG. 4 is a perspective view of a compressing member of the device embodiment shown in FIG. 1.

FIG. 4 is a perspective view of a compressing component 135. The compressing component 135 includes, in one non-limiting embodiment, an opening 135a, (or in other embodiments, a notch, for example), to receive a plunger interfacing tab 143 (shown in FIG. 6B-C). The plunger interfacing tab 143 may be a component of the compressing component 135 in another non-limiting embodiment. The compressing component 135 may also include a protrusion, in one non-limiting embodiment for interfacing with the reset biasing member 133. The compressing component 135 includes a compressing component upper surface 135c for interfacing with the flat biasing member 137 when the device 100 is in a pre-use position, prior to full extension of the plunger 124. The compressing component 135 is configured to compress and deform the flat biasing member 137 when the shield 124 is in a retracted position.

FIG. 5A is a perspective view of a flat biasing member 137 having a body portion 137a and locking arms 137b. FIG. 5B show the flat biasing member in a deformed state, wherein pressure is exerted (as shown in FIG. 5B) on the flat biasing member body portion 137a, causing the locking arms 137b to move inward toward the center of the flat biasing member 137 as shown in FIG. 5B. A release of the pressure on the body portion 137a causes the locking arms 137b to move outward away from the body 137a as shown in FIG. 5A.

Figure 6A:
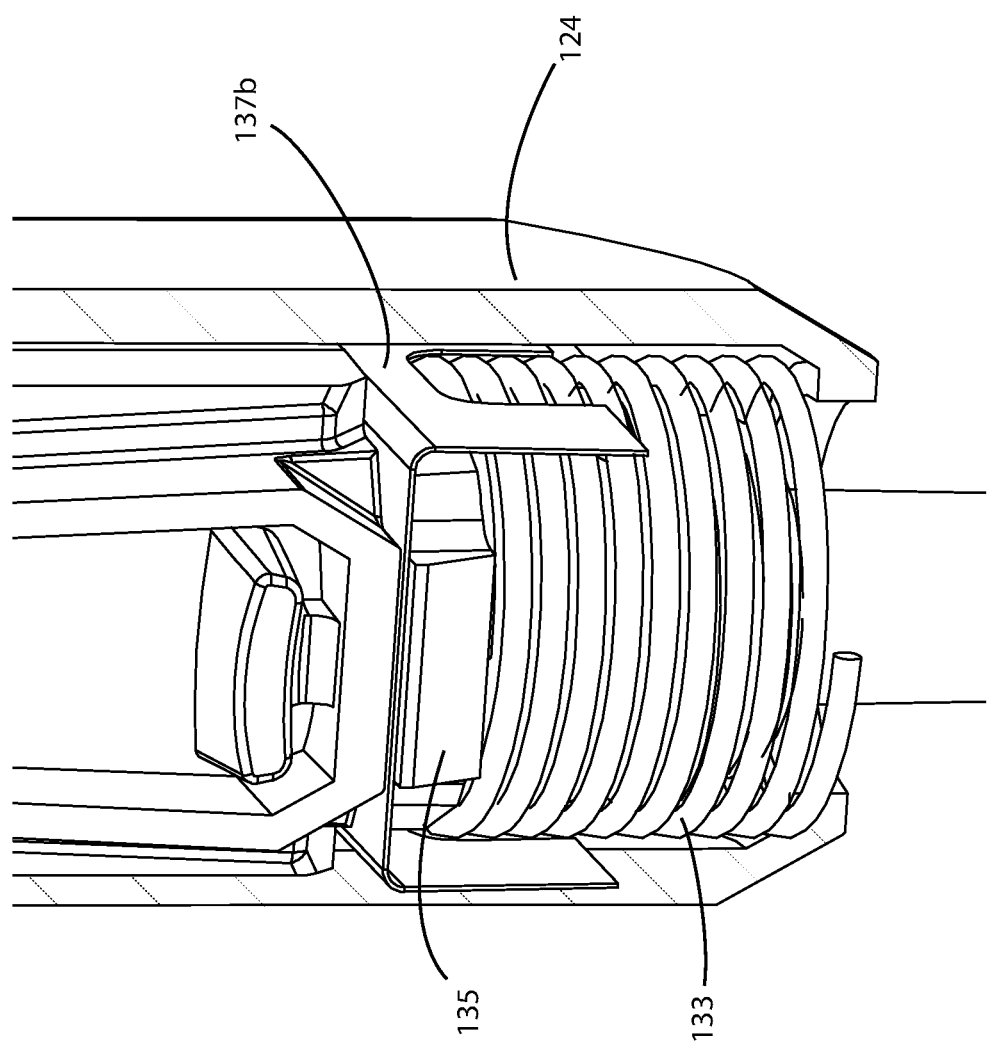
FIG. 6A is a side view of a portion of the device embodiment shown in FIG. 1.
Figure 6C:
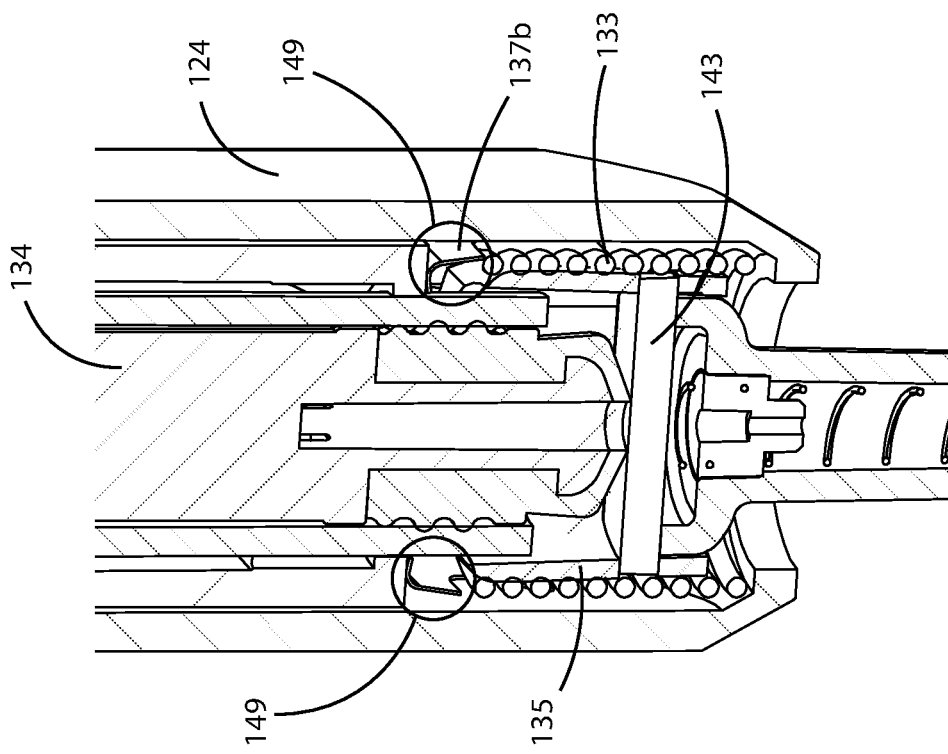
FIGS. 6B-6C include cross sectional views of the view of the device embodiment, shown in FIG. 6A, in operation.

In FIG. 6A, the plunger 134 has been moved distally during use of the device 100. Upon distal movement of the plunger 134, the plunger contacts the plunger interfacing tab 143. Upon distal movement of the plunger 134, a plunger contact region 140 at the proximal end of the plunger 134 is adapted to contact one or more arms 130 of the shield 124 disposed at the proximal end thereof. Therefore, contact between the contact region 140 of the plunger and the one or more arms 130 of the shield releases the arm locking surface 132 of each of the one or more arms 134 from the housing locking surface 122 to release the shield 124 allowing it to extend via the reset biasing member 133. Extension of the shield 124 to a fully extended position deters access to the injection simulation member 120 in a non-limiting embodiment. In some embodiments, the distal end of the plunger 134 may include or be coupled to a stopper. Movement of the plunger toward the distal end 114 of the housing 110 simulates movement of a plunger in a drug delivery-needle containing medicament delivery device to deliver medicament from the device. Movement of the plunger 134 toward the distal end 142 of the housing 110 causes the contact region 140 to contact the one or more arms 130 of the shield 124, as aforementioned, causing lateral movement of the arms 130 and releasing the arm locking surface 132 of each arm from the housing locking surface 122 as shown in FIGS. 2-3. Release of the arm locking surface 132 from the body locking surface 122 unlocks the shield 124, allowing the shield 124 to be released from the pre-use, locked position. The force of the resetting biasing member 133 on the distal portion of the shield 115 causes the shield to extend over the injection simulation member 120 once the device 100 is removed from a target surface.

Figure 6B:
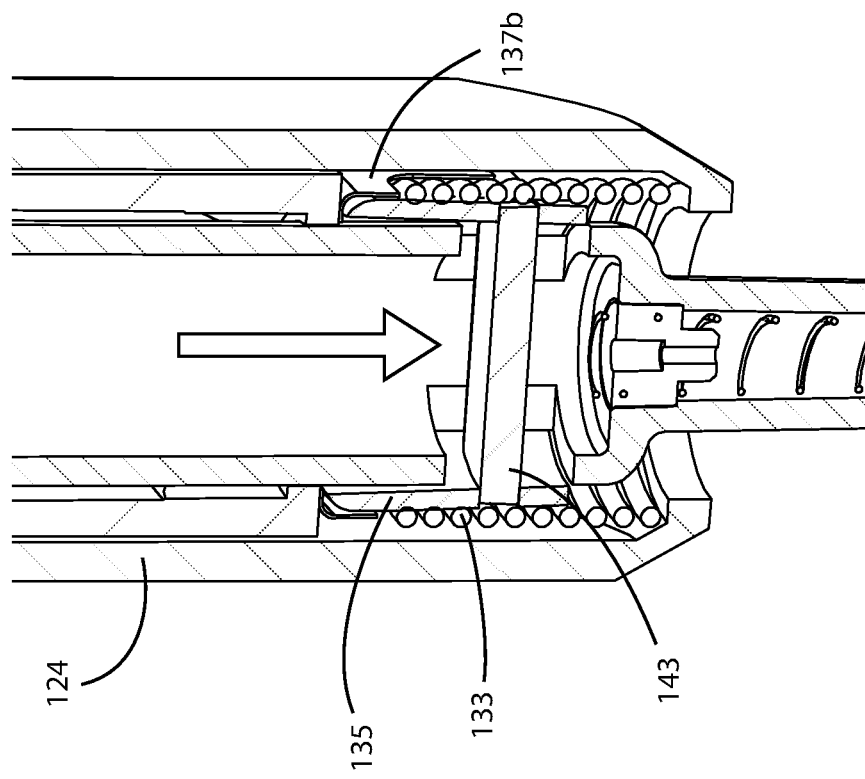

Distal movement of the plunger 134 compresses the reset biasing member 133 (prior to release of the shield 124 via the arm locking surface 132 and housing locking surface 122) as shown in FIG. 6B-6C, and the interface between the plunger 134 and the plunger interfacing tab 143 moves the compressing component 135 distally as shown from FIG. 6B to FIG. 6C, and away from the flat biasing member 137. This movement releases the pressure of the compressing component 135 on the flat biasing member body 137a, allowing the flat biasing member locking arms 137b to move toward the walls of the shield 124 as shown in FIG. 6C. FIG. 6C shows a gap 149 created between the flat biasing member 137 and the compressing component 135. FIG. 6A also shows the reset biasing member 133 in a compressed position, and the flat biasing member 137 in a relaxed position, with locking arms 137b outwardly extended toward the walls of the shield 124. FIG. 6C is a cross sectional view of the device embodiment 100 shown in FIG. 6A.

Figure 7B:
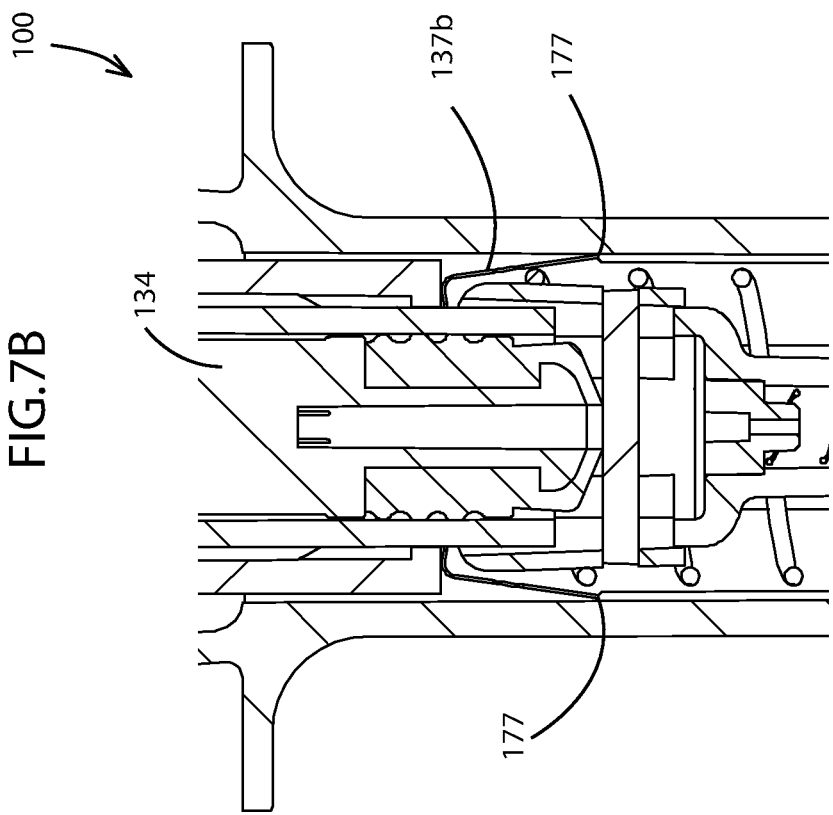
FIG. 7B is a cross sectional view of the device embodiment shown in FIG. 7A.
Figure 7A:
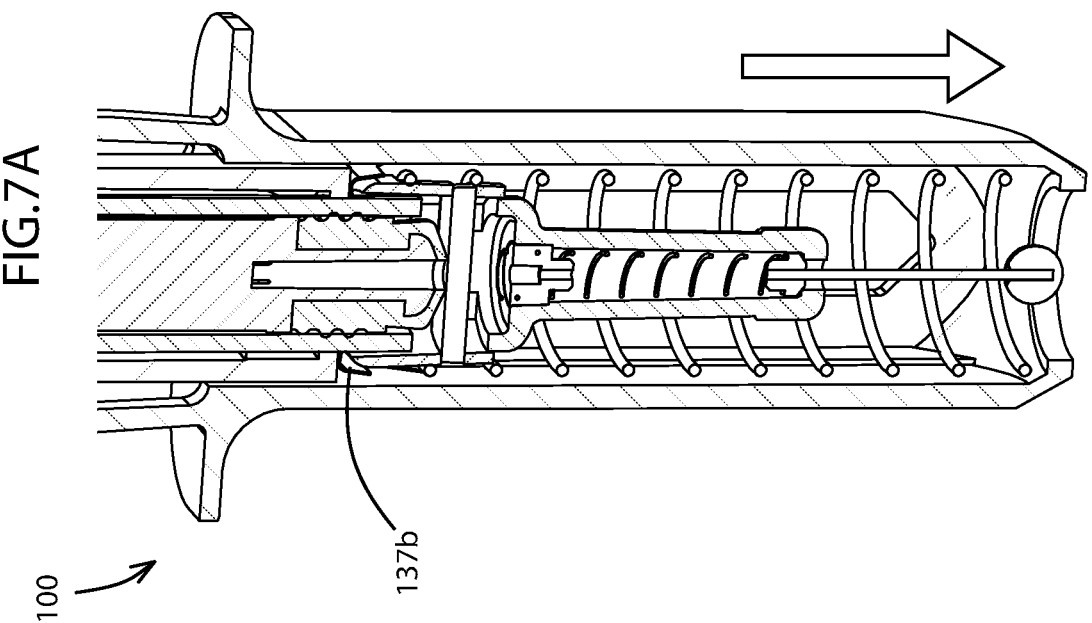
FIG. 7A is a side view of a portion of an embodiment of the device housing in operation.
Figure 8B:
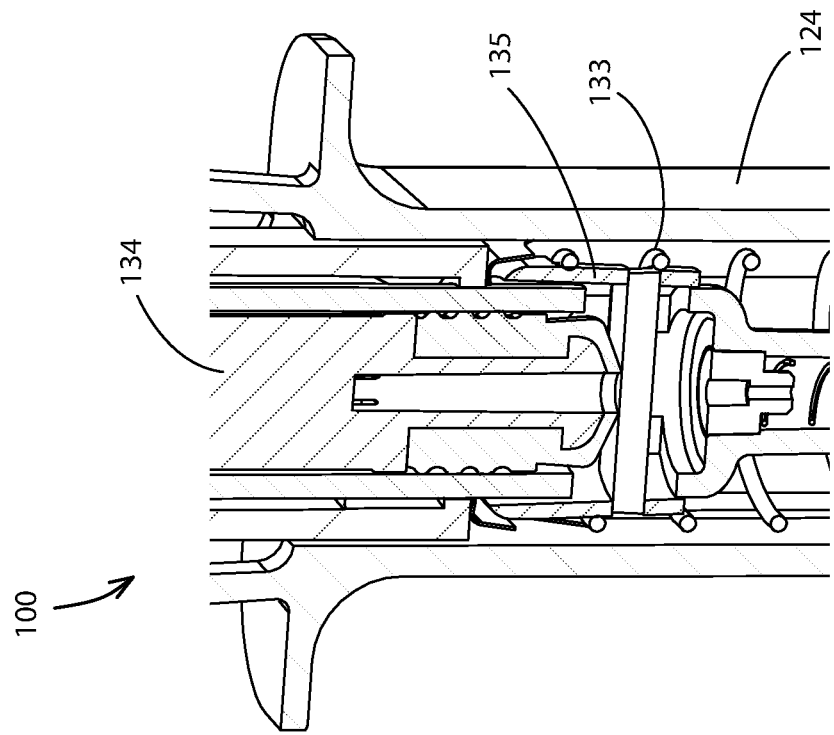
FIG. 8B is a cross sectional view of the embodiment shown in FIG. 8A.
Figure 8A:
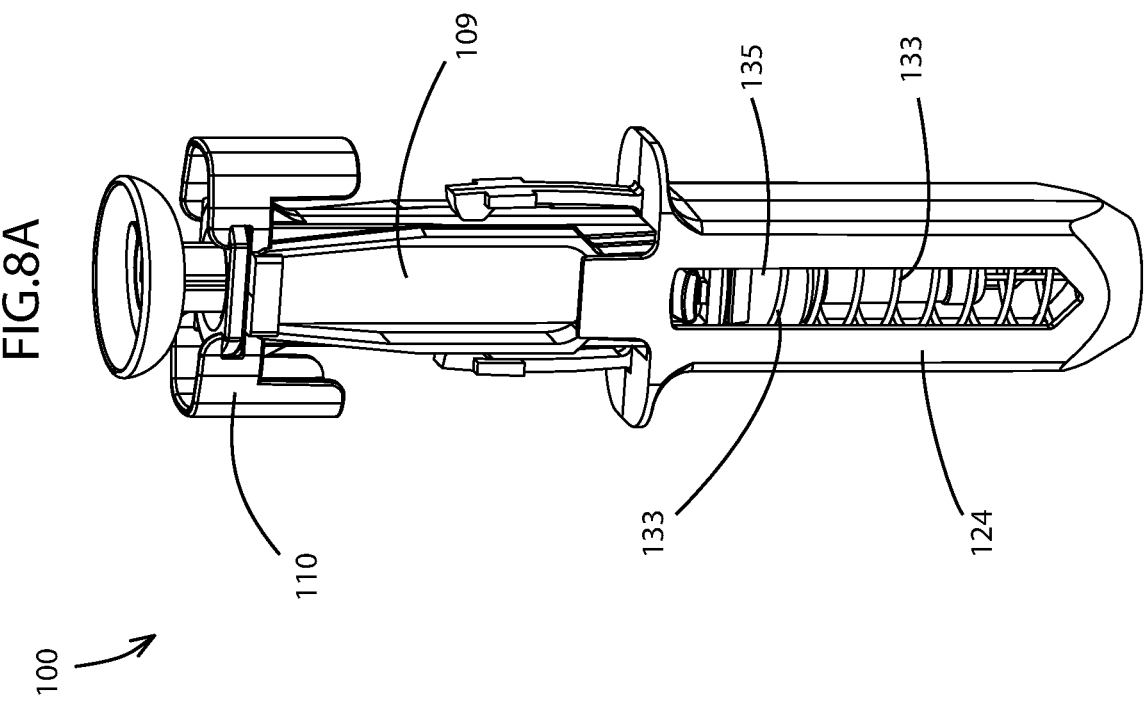
FIG. 8A is a side view of an embodiment of the device shown in FIG. 7A.

FIGS. 7A-B show the embodiment 100 wherein the shield 124 has shifted distally over the injection simulation member 120. As aforementioned, an interface between the contact region 140 of the plunger and the one or more arms 130 of the shield 124 upon distal movement of the plunger 134 releases the arm locking surface 132 of each of the one or more arms 134 from the housing locking surface 122 to release the shield 124 allowing it to extend via the reset biasing member 133. Once the shield 124 reaches a fully extended position as shown in FIGS. 7A-B, the notches 177 on the inner shield surface may interface with the flat biasing member locking arms 137b, which are in an extended position to prevent proximal movement of the shield 124, i.e., to lock the shield 124 in an extended post-use position. The interface between the notches 177, and the flat biasing member 137 locks the shield 124 in the extended position following use of the device 100 until reset of the device 100 to a pre-use position. As can be seen in FIGS. 7A-7B and 8A-8B the resetting biasing member 133 is extended, allowing the shield 124 to extend fully. FIG. 8A-8B include a view of the device embodiment 100, wherein the plunger 134 is in a fully extended position, the shield 124 is in a fully extended, post use position over the injection simulation member 120 with the reset biasing member 133 fully extended. In this view the inner housing portion 109 associated with the housing 110 is visible. FIGS. 8A-8B show the post use position of the device embodiment 100 with the shield 124 in a fully extended, locked position.

FIGS. 9A-B demonstrate a first step in reset of the device 100, which occurs by release of the shield 124 from its extended, locked position, and reset of the shield 124 to its pre-use position in preparation for a subsequent use of the device 100. In order to reset the device 100, the plunger 134 is retracted, (i.e., the plunger 124 is moved proximally relative to the device 100) as shown in FIGS. 9A-B. Due to the interrelation between the inner housing portion 109, the plunger interfacing tab 143, and the compressing component 135, the compressing component 135 is also moved in a proximal direction relative to the device 100. As described above, the compressing component 135 may include an opening 135a for receiving at least a portion of the plunger interfacing tab 143. The tab 143, in one embodiment, is movable between a first position and a second position relative to the inner housing portion 109. The first position of the tab 143 is the most proximal position, shown in FIG. 6B prior to the application of force by the plunger 134 on the tab 143, and the most distal position of the tab 143 is shown in FIG. 6C when the plunger 134 force is acting on the tab 143.

During reset, this proximal plunger 124 movement may cause the compression component 135 to interface with the flat biasing member 137, which may deform the flat biasing member 137. This deformation of the flat biasing member 137 causes the locking arms 137b to move inward, releasing the locking arms 137b from the notches 177, and unlocking the shield 124, such that it can be moved proximally relative to the device for reset. The deformation of the flat biasing member 137 allows the notches 177 to slide past the locking arms 137 during reset (proximal movement) of the shield 124, exposing the injection simulation member 120 for a subsequent use of the device 100. To fully reset the device 100, the shield 124 may be moved proximally relative to the housing 110 until the arm locking surface 132 of the one or more arms 130 of the shield and the housing locking surface 122 interface to maintain the shield 124 in a pre-use position.

In non-limiting embodiments, portions of the housing 110 or the inner housing 109 or the shield 124 may include transparent portions to allow a user to see the contents of the device 100, and, in one particular embodiment, to provide a view into the cavity 116. In an alternative embodiment, the housing 110 may include an opening providing a view into the contents of the housing 110. These features may allow a user to determine an amount of fluid in inner housing 109, for example, during use of the device in embodiments where a fluid is contained there within. In other embodiments, the transparent portion or window may allow a user to see the location of one or more components of the device to determine the position of the components during use of the device 100.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A resettable injection training device, comprising:
a housing comprising a proximal end and a distal end, the housing defining a cavity;
a plunger slidable relative to the housing between the proximal end and the distal end;
a releasably locking shield comprising a proximal end and a distal end, the shield being slidably engaged with the housing and movable between a retracted, pre-use position and an extended, post-use position;
a flat biasing member comprising one or more locking arms for locking the shield in the extended, post-use position;
a compressing component, said compressing component slidable relative to the housing;
wherein the compressing component exerts a pressure on the flat biasing member to deform the flat biasing member and maintain its locking arms away from the safety shield, and wherein distal movement of the plunger releases the compressing component from the flat biasing member, allowing the locking arms to extend toward the safety shield, and lock the shield in an extended, post-use position.

2. The resettable injection training device of claim 1, wherein the shield comprises one or more notches on an inner surface thereof for interfacing with the one or more locking arms to lock the shield in an extended position upon release of the compressing component from the flat biasing member and extension of the shield.

3. The resettable injection training device of claim 2, wherein the one or more locking arms interface with the notches to prevent proximal movement of the shield.

4. The resettable injection training device of claim 3, wherein proximal movement of the plunger moves the compressing component proximally to deform the flat biasing member, releasing the locking arms from the notches, and releasing the shield from the extended, locked position.

5. The resettable injection training device of claim 4, wherein proximal movement of the shield resets the shield to a pre-use position.

6. The resettable injection training device of claim 1, further comprising a resetting biasing member associated with the compressing component and the shield, wherein extension of the resetting biasing member extends the shield to the extended, post-use position.

7. The resettable injection training device of claim 1, further comprising an injection simulation member associated with the distal end of the device, the injection simulation member configured to simulate an injection member of a medicament delivery device.

8. The resettable injection training device of claim 1, wherein distal movement of the plunger releases the compressing component from the flat biasing member.

9. The resettable injection training device of claim 1, wherein the shield further comprises one or more arms at its proximal end each having an arm locking surface, and wherein the housing comprises a housing locking surface at its proximal end, the arm locking surface configured to interface with the housing locking surface when the shield is in a retracted position.

10. The resettable injection training device of claim 9, wherein distal movement of the plunger causes an interface between the plunger and the one or more arms of the shield, releasing the shield from the retracted position.

11. A method for resetting a resettable injection training device having an extended, locked shield, a housing, a plunger disposed and slidable within a cavity of the housing, and a compressing component for interfacing with a locking member having locking arms, comprising:
   sliding the plunger in a proximal direction to retract the plunger, causing the compressing component to interface with the locking member, causing the locking arms to release contact with the shield;
   sliding the shield from the extended position to a retracted position.

12. The method of claim 11, wherein the shield further comprises at least one arm component, the arm component comprising a locking surface configured to interface with a locking surface on the housing when the shield is in a retracted position, such that sliding the shield to a fully retracted position causes the arm component locking surface to interface with the housing locking surface to maintain the shield in a retracted position for a subsequent use of the device.

13. The method of claim 11, wherein the shield comprises one or more notches to interface with the one or more locking arms of the locking member, to lock the shield in an extended position.

14. The method of claim 11, wherein proximal movement of the plunger causes an interface between the compressing component and the locking member, which deforms the locking member releasing the one or more locking arms from the shield to unlock the shield.

* * * * *